United States Patent [19]

Finter et al.

[11] Patent Number: 4,564,578
[45] Date of Patent: Jan. 14, 1986

[54] NOVEL THIOXANTHONES SUBSTITUTED BY ALPHA-AMINOALKYL GROUPS

[75] Inventors: Jürgen Finter, Freiburg, Fed. Rep. of Germany; Walter Fischer, Reinach, Switzerland

[73] Assignee: Ciba-Geigy Corporation, Ardsley, N.Y.

[21] Appl. No.: 551,761

[22] Filed: Nov. 14, 1983

[30] Foreign Application Priority Data

Nov. 25, 1982 [CH] Switzerland .................. 6873/82

[51] Int. Cl.$^4$ .................. G03C 1/68; G03C 1/70; G03C 1/71; C07C 87/28
[52] U.S. Cl. .................. 430/270; 430/280; 430/298; 430/922; 430/315; 204/159.18; 204/159.24; 549/27
[58] Field of Search ............ 430/280, 298, 922, 270, 430/315; 549/27; 204/159.18, 159.24

[56] References Cited

U.S. PATENT DOCUMENTS

| | | | |
|---|---|---|---|
| 3,827,957 | 8/1974 | McGinniss | 204/159.24 X |
| 3,926,643 | 12/1975 | Chang | 430/922 X |
| 3,959,547 | 5/1976 | Polichette et al. | 428/209 |
| 4,105,518 | 8/1978 | McGinniss | 204/159.18 X |
| 4,220,707 | 9/1980 | Ohmura et al. | 430/280 X |
| 4,385,182 | 5/1983 | Fischer et al. | 430/915 |

FOREIGN PATENT DOCUMENTS 769480 10/1980 U.S.S.R. .................. 430/280

OTHER PUBLICATIONS

Fischer et al., *Chemical Abstracts*, vol. 96, May 3, 1982, Columbus, Ohio, USA, Abstract No. 143533u.

*Primary Examiner*—John E. Kittle
*Assistant Examiner*—Cynthia Hamilton
*Attorney, Agent, or Firm*—Michael W. Glynn

[57] ABSTRACT

The novel thioxanthones of the formula I

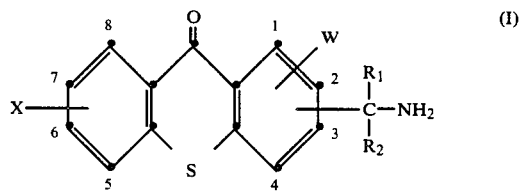

in which $R_1$, $R_2$, X and W are as defined in patent claim 1, are suitable, for example, for the preparation of photosensitive, compositions of matter which are capable of undergoing condensation or addition reactions and may or may not be crosslinkable, and which in turn are used for image formation, in particular by means of electroless deposition of metals. Such compositions of matter contain, for example, a thioxanthone of the formula I, an oligomer or polymer with terminal glycidyl groups and, where relevant, a crosslinking agent and/or a salt of a metal or group Ib or VIII of the Periodic Table.

13 Claims, No Drawings

NOVEL THIOXANTHONES SUBSTITUTED BY ALPHA-AMINOALKYL GROUPS

The present invention relates to novel thioxanthones which are substituted by α-aminoalkyl groups, processes for their preparation and the novel intermediates thereby obtainable, and the use of the novel thioxanthones, in particular in photosensitive compositions of matter which are capable of undergoing condensation or addition reactions.

Novel useful thioxanthones, substituted by α-aminoalkyl groups, of the formula I

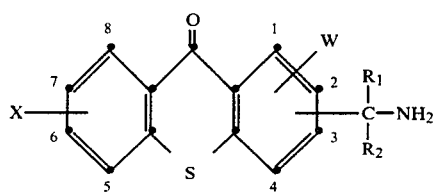
(I)

in which X is hydrogen, chlorine, bromine, $C_{1-4}$-alkyl or $C_{1-6}$-alkoxy, $R_1$ is hydrogen, $C_{1-6}$-alkyl, phenyl, —COOCH$_3$ or —COOC$_2$H$_5$ and $R_2$ is hydrogen, $C_{1-6}$-alkyl, —COOCH$_3$ or —COOC$_2$H$_5$, or $R_1$ and $R_2$ together are —(CH$_2$)$_e$—, where e=4 or 5, and W is hydrogen or —COOC$_{1-4}$-alkyl, have been found.

Chlorine or bromine atoms and alkyl or alkoxy groups X are preferably bonded in the 7-position.

Alkyl groups X, $R_1$ and $R_2$ are straight-chain or branched groups, for example methyl, ethyl, n-propyl, isopropyl, n-butyl, sec.-butyl, tert.-butyl, n-pentyl, 2- or 3-pentyl, n-hexyl and 2-ethylhexyl. Alkyl groups X, $R_1$ and $R_2$ are preferably straight-chain and have, in particular, 1 or 2 C atoms. The alkyl moiety in a —COOC$_{1-4}$-alkyl group W can likewise be straight-chain or branched, and is an alkyl group of the abovementioned type. —COOCH$_3$ and —COOC$_2$H$_5$ are preferred.

Alkoxy groups X are straight-chain or branched groups, such as the methoxy, ethoxy, n-propoxy, isopropoxy, n-butoxy, sec.-butoxy, n-pentyloxy and n-hexyloxy group. Straight-chain alkoxy groups having 1–4, in particular 1 or 2, C atoms are preferred.

$R_1$ and $R_2$ are preferably identical groups.

The group —C($R_1$)($R_2$)—NH$_2$ is preferably bonded in the 2-, 3- or 4-position. Preferred compounds of the formula I are those in which X is hydrogen or chlorine or methyl bonded in the 7-position, the group —C($R_1$)($R_2$)—NH$_2$ is bonded in the 2-, 3- or 4-position, $R_1$ and $R_2$ independently of one another are hydrogen, methyl, ethyl, —COOCH$_3$ or —COOC$_2$H$_5$ and W is hydrogen, —COOCH$_3$ or —COOC$_2$H$_5$. Particularly preferred compounds of the formula I are those in which X is hydrogen or methyl bonded in the 7-position, the group —C($R_1$)($R_2$)—NH$_2$ is bonded in the 2- or 3-position, $R_1$ and $R_2$ are each hydrogen or methyl and W is hydrogen, —COOCH$_3$ or —COOC$_2$H$_5$. 2-Aminomethylthioxanthone, 3-(2-amino-2-propyl)-thioxanthone, 3-(2-amino-2-propyl)-7-methylthioxanthone and ethyl 3-(2-amino-2-propyl)-thioxanthone-1-carboxylate are very particularly preferred.

The compounds of the formula I can be prepared by methods which are known per se, for example as follows:

(a) Compounds of the formula I in which $R_1$ is other than hydrogen: by reacting a compound of the formula II

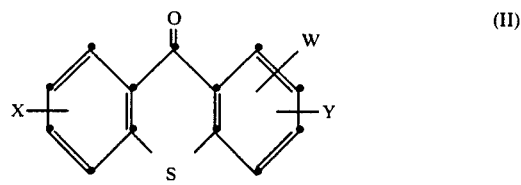
(II)

with a compound of the formula III

(III)

to give a compound of the formula IV

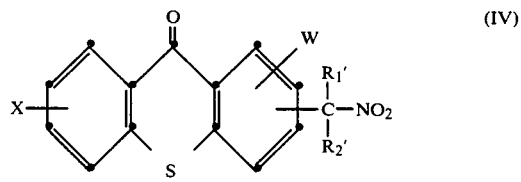
(IV)

and reducing the compound of the formula IV to a compound of the formula I in which $R_1$ is other than hydrogen. This process is particularly suitable for the preparation of compounds of the formula I in which the group —C($R_1$)($R_2$)—NH$_2$ is bonded in the 1-position or, in particular, in the 3-position.

(b) Compounds of the formula I in which $R_1$ and $R_2$ independently of one another are —COOCH$_3$ or —COOC$_2$H$_5$: by reacting a compound of the formula II with a compound of the formula Va or Vb

HC($R_1''$)($R_2''$)—NH$_2$     (Va)

or

HC($R_1''$)($R_2''$)—NHCOCH$_3$     (Vb)

in the presence of a base to give a compound of the formula Ia or VI

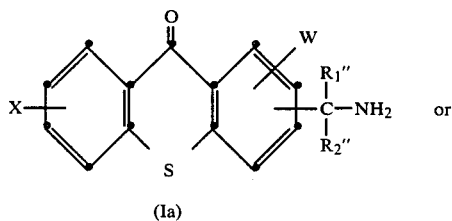
(Ia)

or

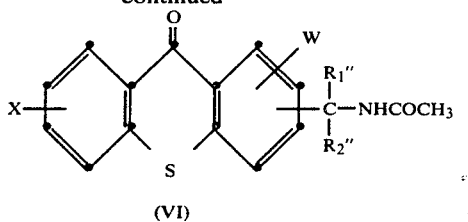

(VI)

and hydrolysing the compound of the formula VI to give a compound of the formula Ia in which $R_1''$ and $R_2''$ independently of one another are —COOCH$_3$ or —COOC$_2$H$_5$, but are preferably identical.

(c) Compounds of the formula I in which R$_1$ or R$_1$ and R$_2$ are hydrogen: by reacting a compound of the formula VII

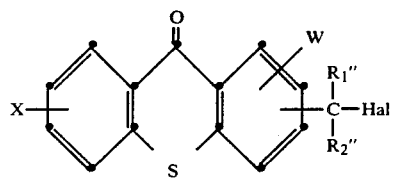

(VII)

with an azide of the formula VIII

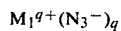 (VIII)

to give a compound of the formula IX

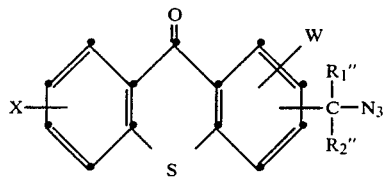

(IX)

and reducing the compound of the formula IX to a compound of the formula I in which R$_1$ or R$_1$ and R$_2$ are hydrogen.

In these formulae, R$_1$, R$_2$, X and W are as defined under formula I, Y is bromine, chlorine, fluorine or —NO$_2$, R$_1'$ and R$_2'$ have the same meaning as R$_1$ and R$_2$, but R$_1'$ is other than hydrogen, R$_1''$ and R$_2''$ independently of one another are —COOCH$_3$ or —COOC$_2$H$_5$, R$_1'''$ is hydrogen and R$_2'''$ has the same meaning as R$_2$, or R$_1'''$ and R$_2'''$ are both hydrogen, Hal is a halogen atom, in particular bromine or chlorine, M$^+$ is the cation of an organic or inorganic base, q is 1 or 2 and M$_1^+$ is an alkali metal, alkaline earth metal or quaternary ammonium cation.

The reaction of the compounds of the formula II with the salts of the formula III is advantageously carried out in the presence of an inert organic solvent. Examples of suitable solvents are dialkylsulfoxides, such as dimethyl- and diethyl-sulfoxide, N,N-dialkylamides of aliphatic monocarboxylic acids having 1–3 C atoms in the acid moiety, such as N,N-dimethylformamide and N,N-dimethylacetamide, cyclic amides, such as N-methylpyrrolidone, and hexamethylphosphoric acid triamide.

The salts of the formula III can be used as such or can be formed in situ from a compound HC(R$_1$)(R$_2$)—NO$_2$ and a suitable organic or inorganic base. M$^+$ is, for example, an alkali metal, alkaline earth metal or ammonium cation, such as a trialkyl, benzyltrialkyl or tetraalkylammonium cation having in each case 1–12, and in particular in each case 1–4, C atoms in the alkyl moieties. M$^+$ is preferably an alkali metal cation, in particular the sodium or potassium cation. If the salt of the formula III is formed in situ, examples of compounds which can be used are tertiary amines, such as triethylamine, quaternary ammonium salts, such as tetramethyl-, tetraethyl-, benzyltrimethyl- and benzyltriethylammonium salts, and alkali metal or alkaline earth metal carbonates, hydroxides or halides, such as sodium and potassium carbonate, sodium and potassium hydroxide and sodium, potassium or lithium fluoride. Formation of the salts of the formula III in situ, in particular using sodium carbonate or potassium carbonate, is preferred.

The reduction of the compounds of the formula IV to the compounds of the formula I can be carried out in a manner which is known per se, for example in the presence of HCL, or acetic acid and iron, or acetic acid and zinc, under reflux conditions, or catalytically, in particular in the presence of platinum catalysts or palladium catalysts and an inert organic solvent, for example dioxane, N,N-dimethylformamide, methanol or ethanol.

Examples of suitable bases for the reaction of the compounds of the formula II with the compounds of the formula Va or Vb are sodium carbonate and potassium carbonate. Hydrolysis of the compounds of the formula VI to give the compounds of the formula Ia is advantageously carried out in an acid medium, for example with the addition of concentrated HCl.

A quaternary ammonium cation M$_1^+$ in formula VIII is, for example, a tetraalkyl- or benzyltrialkyl-ammonium cation having in each case 1–12, and in particular 1–4, C atoms in the alkyl moieties, especially the tetramethyl- or trimethylbenzyl-ammonium cation. Examples of suitable alkali metal or alkaline earth metal azides of the formula VIII are lithium, sodium, potassium, calcium, magnesium and barium azide. Alkali metal azides are preferably used, in particular sodium azide.

The reaction of the compounds of the formula VII with the azides of the formula VIII is advantageously carried out in the presence of an inert organic solvent, such as N,N-dimethylformamide, N,N-dimethylacetamide, dimethylsulfoxide, N-methylpyrrolidone or hexamethylphosphoric acid triamide. Preferred solvents are dimethylsulfoxide, N,N-dimethylformamide and N,N-dimethylacetamide.

The reduction (hydrogenation) of the compounds of the formula IX to compounds of the formula I can be carried out in a manner which is known per se. Examples of suitable reducing agents are complex hydrides, such as sodium borohydride and lithium aluminium hydride, hydrazine and alkali metal sulfides. Catalytic hydrogenation is preferred, and known hydrogenation catalysts can be used. Noble metal catalysts, such as platinum, rhodium, palladium, ruthenium or iridium catalysts, are particularly suitable. Platinum-on-charcoal and palladium-on-charcoal catalysts are particularly preferred.

2-Aminomethylthioxanthone can also be prepared in accordance with the following equation:

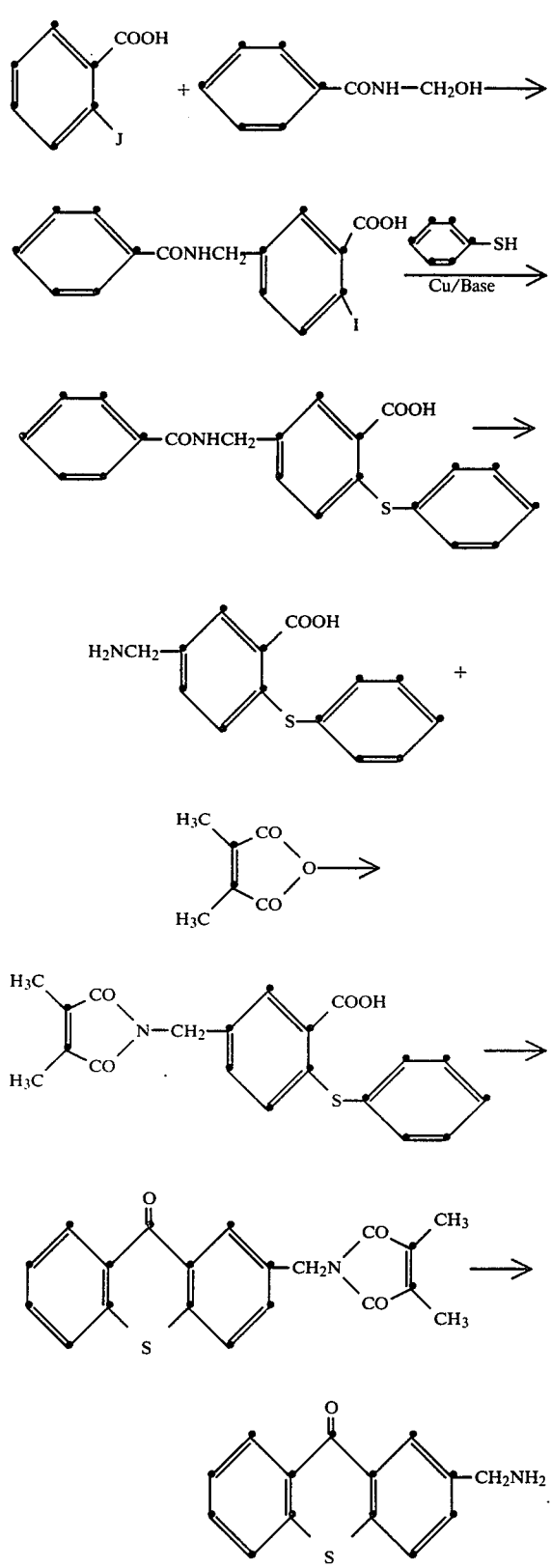

Finally, the intermediates of the formula IV can also be prepared by nitrating compounds of the formula X

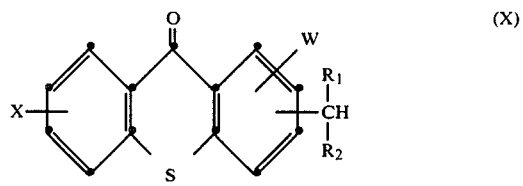

with nitric acid. However, nitration of the benzene rings also occurs in some cases. The resulting compositions of matter can be separated, for example by chromatography. In formula X, X, W, $R_1$ and $R_2$ are as defined under formula I.

The intermediates of the formula IV where W=hydrogen which have been developed for the preparation of the compounds of the formula I, and the intermediates of the formula IX are novel and are likewise the subject of the present invention. The above statements in respect of preferred meanings of X and W and preferred positions of the —C($R_1'''$)($R_2'''$)—$N_3$ or C($R_1'$)($R_2'$)—$NO_2$ group apply. $R_1'''$ and $R_2'''$ are preferably each hydrogen.

The starting substances of the formulae II, III, IV, where W=—COO$C_{1-4}$-alkyl, Va, Vb, VII, VIII and X are known, or they can be prepared by methods which are known per se. Compounds of the formula II and X can be obtained, for example, by processes analogous to those described in German Offenlegungsschrift No. 3,117,568-A 1, whilst compounds of the formula VII can be prepared according to Rev. Chim. (Bukarest), 19, 561 (1968).

The compounds of the formula I are used, for example, in photosensitive compositions of matter, in particular for image formation. The invention thus also relates to novel photosensitive compositions of matter which are capable of undergoing condensation or addition reactions and may or may not be crosslinkable, containing (1) a thioxanthone of the formula I, (2) one or more compounds selected from di- to polyglycidyl ethers of phenol novolaks and cresol novolaks and compounds of the formulae XI to XIII

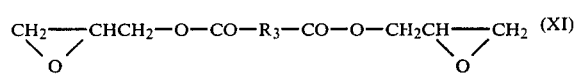

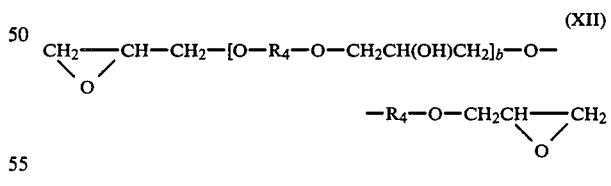

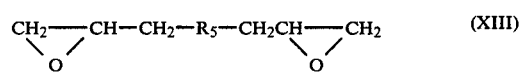

and, if appropriate, compounds of the formulae XIV, XV and/or XVI

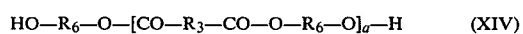

and/or $$HOOC-R_3-CO-[O-R_6-O-CO-R_3-CO]_a-OH \quad (XVI)$$

the proportion of compounds of the formulae XIV, XV and/or XVI being at most 80 mole %, based on all the reactants mentioned under (2), (3) if appropriate, a crosslinking agent and (4) if appropriate, a salt of a metal of group Ib or VIII of the Periodic Table, in which a is a number from 1 to 100, in particular 2 to 50, b is a number from 0 to 150, in particular 0.1 to 150 and especially 2 to 100, $R_3$ is a direct bond, $-C_mH_{2m}-$, where m=2-12, or cyclohexylene, cyclohexenylene, phenylene or endomethylenecyclohexenylene, each of which can be substituted by a methyl group, $R_4$ is $-C_mH_{2m}-$, where m=2-2, phenylene, or a group of the formula

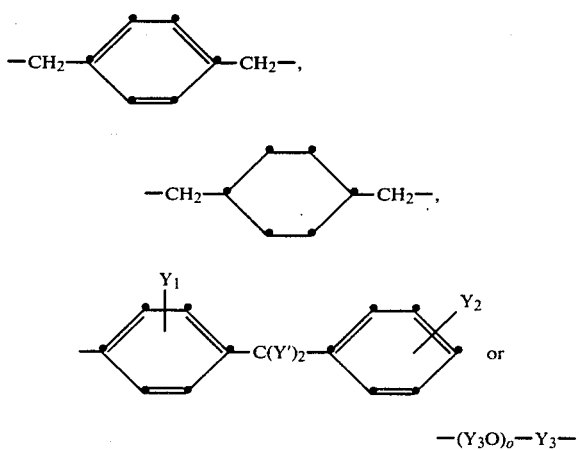

Y' is hydrogen or methyl, $Y_1$ and $Y_2$ independently of one another are hydrogen, chlorine or bromine, $Y_3$ is $-(CH_2)_2-$, $-CH_2CH(CH_3)-$ or $-(CH_2)_4-$, o is a number from 1 to 50, $R_5$ is

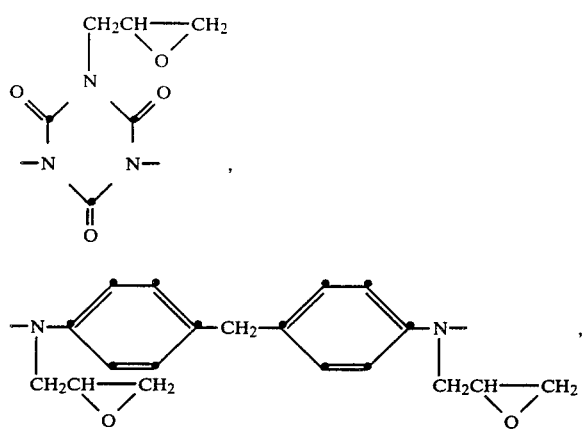

or the radical of ethylene-urea, 1,3-propylene-urea, 5,5-dimethylhydantoin, 2-hydroxyethyl-5,5-dimethylhydantoin or 2-hydroxypropyl-5,5-dimethylhydantoin and $R_6$ is $-C_mH_{2m}-$, where m=2-12, $-(CH_2(CH_2O)_r-CH_2-CH_2-$, where r=1-40, in particular 1-20, $-CH(CH_3)CH_2OCH_2CH(CH_3)-$, $-CH_2-C(CH_3)_2-OCO-C(CH_3)_2CH_2-$, cyclohexylene,

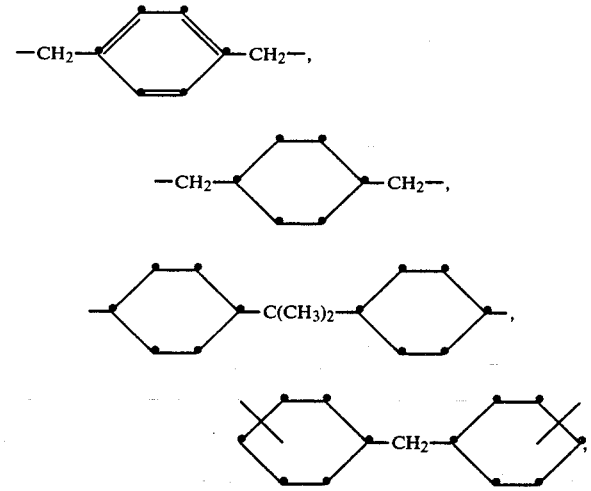

naphthylene or biphenylene, or phenylene which is unsubstituted or substituted by a methyl, methoxy or nitro group.

As defined, the compositions of matter according to the invention must be capable of undergoing condensation or addition reactions. The compounds of the formulae XIV and XV which may or may not be used can react, for example, with the di- to poly-glycidyl ethers of phenol novolaks or cresol novolaks or the compounds of the formulae XI to XIII and XVI.

The proportion of compounds of the formula I is advantageously between 1 and 60 mole %, preferably 2 and 45 mole %, based on the compounds mentioned under (2). If a or b is greater than 1, the individual symbols $R_3$, $R_4$, $R_6$ and $Y_3$ in the compounds of the formulae XII and XIV to XVI (oligomers or polymers) can have identical or different meanings, and recurring structural elements in such oligomers or polymers can be arranged randomly or in the form of blocks.

$-C_mH_{2m}-$ groups $R_3$, $R_4$ or $R_6$ can be straight-chain or branched. Examples of such groups are: $-(CH_2)_2-$, $-CH_2CH(CH_3)-$, $-(CH_2)_3-$, $-(CH_2)_4-$, $-(CH_2)_2-C(CH_3)_2-(CH_2)_2-$, $-(CH_2)_6-$, $-C(CH_3)_2-$, $-CH_2C(CH_3)_2-CH_2-CH(CH_3)(CH_2)_2-$, $-CH_2CH(CH_3)CH(CH_3)CH_2CH(CH_3)CH_2-$, $-(CH_2)_7-$, $-(CH_2)_8-$, $-(CH_2)_{10}-$ and $-(CH_2)_{12}-$.

$-C_mH_{2m}-$ groups $R_4$ and/or $R_6$ are, in particular, radicals of ethylene glycol, butane-1,4-diol, neopentylglycol or hexane-1,6-diol. A $-C_mH_{2m}-$ group $R_3$ is, in particular, a radical derived from succinic acid, adipic acid, pimelic acid, azelaic acid or sebacic acid.

A cyclohexylene radical $R_6$ is, in particular, the radical of cyclohexane-1,2-diol. Cyclohexylene groups $R_3$ are, in particular, 1,3- and, especially, 1,4-cyclohexylene, which can be substituted by methyl, but are preferably unsubstituted.

A naphthylene or biphenylene radical $R_6$ or a phenylene radical $R_6$ which is unsubstituted or substituted by a methyl, methoxy or nitro group is, for example, a radical of 1,4-, 1,6-, 1,8- or 2,6-dihydroxynaphthalene, 2,2'-biphenyl, resorcinol, 2,5-dihydroxyanisole, 1,2-dihydroxy-4-nitrobenzene or 2,5- or 3,4-dihydroxytoluene. $R_6$ is preferably $-(CH_2)_2-$, $-(CH_2)_4-$, $-(CH_2)_6-$, $-CH_2CH_2OCH_2CH_2-$, $-C(CH_3)hd 2-$,

or 1,3-phenylene.

A cyclohexenylene, phenylene or endomethylenecyclohexenylene radical $R_3$ which is unsubstituted or substituted by methyl is, for example, a radical derived from methyltetrahydrophthalic acid, endomethylenetetrahydrophthalic acid, tetrahydrophthalic acid, phthalic acid, isophthalic acid or terephthalic acid. $R_3$ is preferably —$(CH_2)_m$—, where m=2–10, 1,3- or 1,4-phenylene or 1,3- or 1,4-cyclohexylene.

A phenylene radical $R_4$ is, in particular, 1,3-phenylene. In a

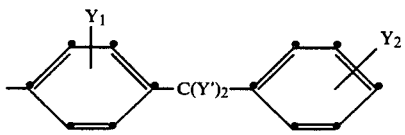

group $R_4$, $Y_1$ and $Y_2$ are preferably each chlorine or bromine bonded in the 2,2'-position. However, those groups in which $Y_1$ and $Y_2$ are hydrogen are particularly preferred. In a —$(Y_3O)_o$—$Y_3$ group $R_4$, $Y_3$ is preferably —$(CH_2)_2$— or —$CH_2CH(CH_3)$— and o is, in particular, 1 to 40, especially 2–20.

$R_4$ is preferably —$C_mH_{2m}$—, where m=2, 4 or 6, or

but in particular a group of the formulae

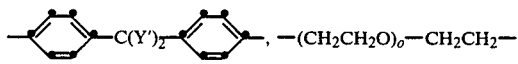, —$(CH_2CH_2O)_o$—$CH_2CH_2$— and/or —$[CH_2CH(CH_3)O]_o$—$CH_2CH(CH_3)$—, where Y'=hydrogen or, in particular, methyl and o=1 to 40, in particular 2–20.

$R_5$ is preferably the radical of 5,5-dimethylhydantoin, 2-hydroxyethyl- or 2-hydroxypropyl-5,5-dimethylhydantoin or triglycidylisocyanurate.

Preferred compositions of matter are those which contain a thioxanthone of the formula I, one or more compounds of the type defined with glycidyl end groups and, if appropriate, a compound of the formula XVI, and, if appropriate, a crosslinking agent and/or a metal salt of the type defined, in which X is hydrogen or chlorine or methyl bonded in the 7-position, the group —$C(R_1)(R_2)$—$NH_2$ is bonded in the 2-, 3- or 4-position, $R_1$ and $R_2$ independently of one another are hydrogen, methyl, ethyl, —$COOCH_3$ or —$COOC_2H_5$ and W is hydrogen, —$COOCH_3$ or —$COOC_2H_5$. Particularly preferred compositions are those which contain one or more compounds of the type defined, with glycidyl end groups, and a thioxanthone of the formula I, and, if appropriate, a crosslinking agent and/or a metal salt of the type defined, in which X is hydrogen or methyl bonded in the 7-position, the group —$C(R_1)(R_2)$—$NH_2$ is bonded in the 2- or 3-position, $R_1$ and $R_2$ are each hydrogen or methyl and W is hydrogen, —$COOCH_3$ or —$COOC_2H_5$.

Particularly preferred compositions are those which contain a compound of the formula I in which X is hydrogen or methyl bonded in the 7-position, the group —$C(R_1)(R_2)$—$NH_2$ is bonded in the 2- or 3-position, $R_1$ and $R_2$ are each H or methyl and W is hydrogen, —$COOCH_3$ or —$COOC_2H_5$, one or more compounds selected from di- and/or tri-glycidyl ethers of phenol novolaks or cresol novolaks, triglycidylisocyanurate, diglycidylhexahydrophthalate, N,N'-diglycidyl-5,5-dimethylhydantoin, N-glycidyl-N'-2-hydroxyethylglycidyl-5,5-dimethylhydantoin and/or N-glycidyl-N'-2-hydroxy-propylglycidyl-5,5-dimethylhydantoin and compounds of the formulae (A), (B) and (C)

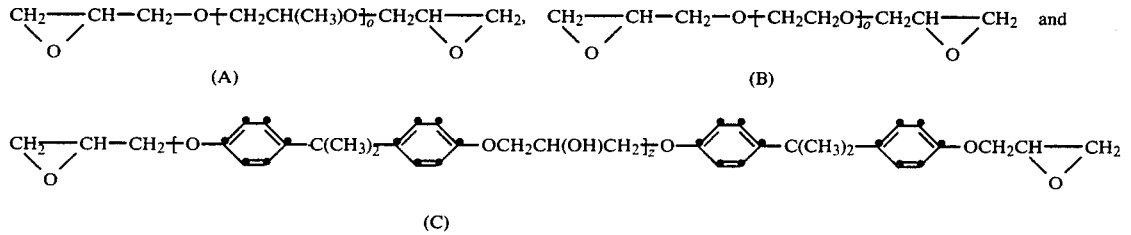 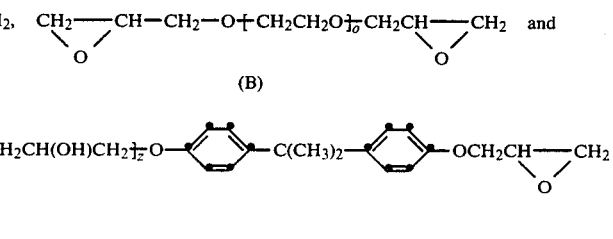

(A) (B)

(C)

and, if appropriate, a crosslinking agent and/or a metal salt of the type defined, in which o equals 2–40, in particular 2–20, and z equals 0.1–13, in particular 2–11.

Very particularly preferred compositions are those which contain, as the compound of the formula I, 2-aminomethylthioxanthone, 3-(2-amino-2-propyl)-thioxanthone, 3-(2-amino-2-propyl)-7-methylthioxanthone or ethyl 3-(2-amino-2-propyl)thioxanthone-1-carboxylate, a compound of the formula (A) or (B) mixed with a compound of the formula (C), and, if appropriate, a crosslinking agent and/or a metal salt of the type defined, or compositions which contain, as the compound of the formula I, 2-aminomethylthioxanthone, 3-(2-amino-2-propyl)-thioxanthone, 3-(2-amino-2-propyl)-7-methylthioxanthone or ethyl 3-(2-amino-2-propyl)-thioxanthone-1-carboxylate, N,N'-diglycidyl-5,5-dimethylhydantoin, N-glycidyl-N'-2-hydroxyethylglycidyl-5,5-dimethylhydantoin and/or N-glycidyl-N'-2-hydroxypropylglycidyl-5,5-dimethylhydantoin mixed with a compound of the formula (C), and, if appropriate, a crosslinking agent and/or a metal salt of the type defined, in which o is 2–20 and z is 2–11.

The invention also relates to the photosensitive reaction products, which may or may not be crosslinked and are obtainable by reacting a compound of the formula I with one or more compounds selected from di- to polyglycidyl ethers of phenol novolaks and cresol novolaks and compounds of the formulae XI to XIII and, if appropriate, compounds of the formulae XIV, XV and/or XVI, the proportion of compounds of the formulae XIV to XVI being as defined above, in the presence or absence of a crosslinking agent and, if appropriate, then at least partly complexing the resulting reaction products with a salt of a metal of group Ib or VIII of the Periodic Table.

Preferred reaction products are those which can be obtained by reacting mixtures of the preferred type defined above in a manner which is known per se. If several compounds of the type defined under (2) are used, the reaction can also be carried out stepwise by prior (poly)addition or (poly)condensation, for example by first reacting the thioxanthone of the formula I with (less than or more than the stoichiometric amount of) a first reaction component of the type defined and then reacting the resulting reaction product with the other reaction component(s) in the presence or absence of a crosslinking agent and/or a metal salt of the type defined. On the other hand, it is also possible first to react different compounds of the type defined under (2) with one another and to react the resulting reaction product with the thioxane of the formula I in a second stage.

Various linkages of the thioxanthone with the compounds mentioned under (2) or with these latter compounds with one another can be achieved, depending on the nature of the reaction components and the reaction sequence and depending on which reaction components are used in more than or less than the stoichiometric amount. Thus, for example, it is possible to prepare polymers containing recurring structural elements of the formula XVII or XVIII

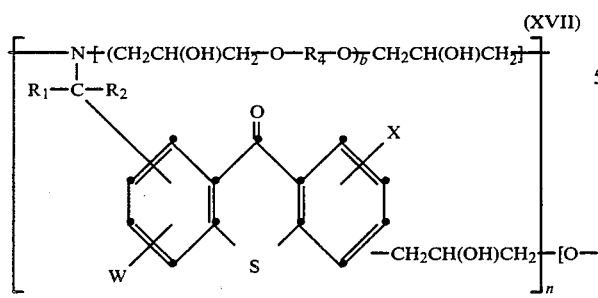

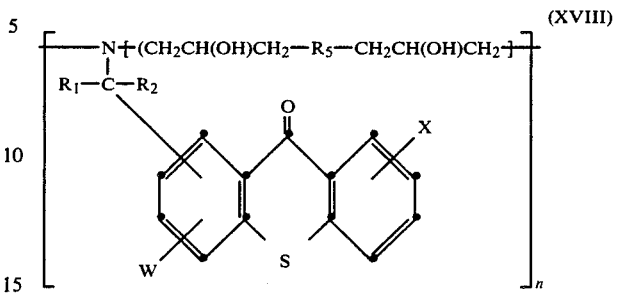

or compounds of the formula XIX or XX

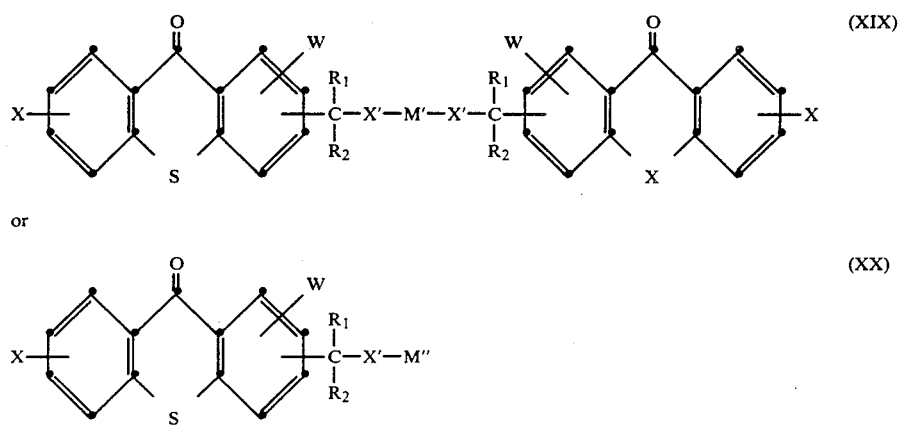

which can be at least partly complexed with metal ions of a metal of group Ib or VIII of the Periodic Table, in which $R_1$, $R_2$, X and W are as defined under formula I, X' is —NH— or —N—, the radicals M' are identical or different radicals of di- to poly-glycidyl ethers of phenol novolaks or cresol novolaks of groupings of the formula XIa, XIIa or XIIIa

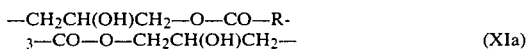

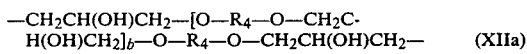

or

and, if X'=—NH—, in some cases, where relevant, a grouping of the formula XVIa

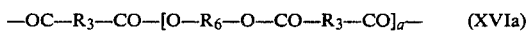

the radicals M" are identical or different groupings of the formula XIIb

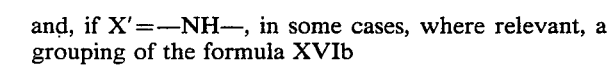

and, if X'=—NH—, in some cases, where relevant, a grouping of the formula XVIb

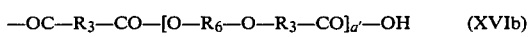

a' is a number from 5 to 100, b' is a number from 5 to 150 and a, b, X, W and $R_1$ to $R_6$ are as defined above.

Linear polymers of the above formulae (X' is other than —N—) preferably have an average molecular weight of 600 to 500,000, in particular 2,000 to 150,000, Daltons. The average molecular weight can be determined by methods which are known per se, for example by means osometry or light scattering.

Under certain circumstances, crosslinked products can also be obtained without the addition of crosslinking agents, for example in the reaction of compounds of the formulae XI to XIII with the thioxanthones of the formula I.

The complexing can be carried out before, after or, preferably, during the application of the compositions of matter or the reaction products obtainable therefrom. Starting polymers which contain metal salts of the type defined can also be used in the preparation of polymers according to the invention.

Salts of metals of the type defined which are suitable for the complexing are those with organic or inorganic acids or mixtures thereof, such as carboxylates, for example formates, acetates, stearates, gluconates and citrates; and halides, nitrates, sulfates and perchlorates. Examples are: iron-III acetate, citrate, gluconate, nitrate, sulfate and perchlorate; iron-II or iron-III chloride and iron-II oxalate; ruthenium-III chloride; cobalt-II acetate, nitrate or sulfate; cobalt-II chloride or bromide; rhodium-II acetate and rhodium-III chloride; nickel-II acetate, nickel-II bromide and chloride and nickel-II sulfate; palladium-II chloride and iodide and palladium acetate and nitrate; copper-II formate and acetate, copper-I and -II chloride, bromide and iodide and copper-II nitrate or sulfate; and silver acetate, chloride, bromide, nitrate or sulfate. Salts of non-noble metals, in particular iron, cobalt, nickel or copper salts, are preferred. Copper salts or $Cu^{++}$ ions are very particularly preferred. Copper-II carboxylates and copper halides are preferred for the complexing. The use of copper-II acetate or mixtures of copper-II acetate and copper-II bromide in a molar ratio of 9:1 is very particularly preferred. The degree of complexing is preferably up to 15%, based on the groups of the polymer or starting substances which are able to undergo complexing. Examples of groups which are able to undergo complexing are OH, NH and secondary amino groups, such as $N(CH_3)_2$ groups.

Examples of crosslinking agents are alcohols, phenols or amines with two or more functional groups, and di-, tri- or tetra-carboxylic acids and derivatives thereof, such as anhydrides, depending on the type of functional groups present. Examples of suitable polyfunctional compounds are: diols HO—$R_4$—OH or HO—$R_6$—OH, dicarboxylic acids HOOC—$R_3$—COOH, oligo-esters of the formula XVI with an average molecular weight of 300–6,000 Daltons, and diamines of the formula $H_2N$—$R_7$—$NH_2$. In these formulae, $R_3$, $R_4$ and $R_6$ are as defined above and $R_7$ is —$C_mH_{2m}$—, where m=2–12, cyclohexylene, naphthylene, phenylene which is unsubstituted or substituted by a methyl, methoxy or nitro group, 1,3- or 1,4-xylylene or the radical of 4,4'-diaminodicyclohexylmethane, 4,4'-diaminodiphenylmethane, 4,4'-diaminodiphenyl ether, 4,4'-diaminodiphenyl sulfone or isophoronediamine. A —$C_mH_{2m}$— radical $R_7$ is preferably —$(CH_2)_2$—, trimethylene, tetramethylene, hexamethylene, —$CH_2CH(CH_3)CH(CH_3)CH_2CH(CH_3)CH_2$— or —$CH_2C(CH_3)_2CH_2CH(CH_3)CH_2CH_2$—.

A naphthylene radical $R_7$ or a phenylene radical $R_7$ which is unsubstituted or substituted by a methyl, methoxy or nitro group is, for example, one of the following radicals: 1,2-, 1,3- or 1,4-phenylene, 4-methoxy-1,3-phenylene, 2-nitro-1,4-phenylene, o- or m-tolylene, 1,5- or 1,8-naphthylene. $R_7$ is preferably —$C_mH_{2m}$—, where m=2–10, 1,3- or 1,4-phenylene or the radical of 4,4'-diaminodiphenylmethane, 4,4'-diaminodiphenyl ether or isophoronediamine. Other crosslinking agents which can be used are: glycerol, tris-(hydroxymethyl)-ethane and -propane, pentaerythritol, diethylenetriamine, triethylenetetramine, succinic anhydride, glutaric anhydride, phthalic anhydride, tetrahydro- and hexahydrophthalic anhydride, trimellitic anhydride, pyromellitic anhydride and benzophenonetetracarboxylic acid dianhydrides. Carboxylic acid anhydrides, such as hexahydrophthalic anhydride or phthalic anhydride, or dihydric or polyhydric alcohols are preferably used for crosslinking compounds containing OH and/or glycidyl groups. Compounds containing glycidyl groups are preferably crosslinked with carboxylic acid anhydrides or dihydric alcohols, in particular hexahydrophthalic anhydride or bisphenol A.

The condensation of ring-opening addition reactions are advantageously carried out in the presence of an inert organic solvent at temperatures between 90° and 160° C., preferably 100° and 130° C. Examples of suitable solvents are chlorobenzene, dichlorobenzenes, N,N-dialkylamides of aliphatic monocarboxylic acids having 1–3 C atoms in the acid moiety, such as N,N-dimethylformamide and N,N-dimethylacetamide, ethylene glycol monomethyl or monoethyl ether, N-methylpyrrolidone and ethylene glycol dimethyl or diethyl ether. If appropriate, the reaction can be carried out in the presence of a catalyst, such as N,N-dimethylbenzylamine.

The photosensitive compositions of matter or reaction products according to the invention are used, for example, as sensitisers (Redox catalysts) in various oxidation/reduction reactions or as coating materials, for example for protecting semiconductor photo-diodes or semiconductor lasers from corrosion. However, they are particularly suitable for image formation by the action of light on various inorganic or organic substrates. Examples of suitable substrates for image formation are glass, metals and metal oxides, such as aluminium, aluminium oxide and copper, ceramics, paper and high molecular weight organic materials. Examples of high molecular weight organic materials are natural and synthetic polymers, for example cellulose materials, such as cellulose acetates, cellulose propionates, cellulose butyrates and cellulose ethers, such as methylcellulose; polymers which are derived from $\alpha,\beta$-unsaturated acids, such as polyacrylates and polymethacrylates, polyacrylamides and polyacrylonitrile; styrene polymers and copolymers thereof, for example styrene/butadiene copolymers and acrylonitrile/butadiene/styrene copolymers; vinyl and vinylidene polymers and copolymers thereof, such as polyvinyl chloride, polyvinylidene chloride, vinyl chloride/vinylidene chloride copolymers and vinyl chloride/vinyl acetate copolymers; polymers which are derived from unsaturated alcohols and amines, and derivatives thereof, such as polyvinyl alcohol, polyvinyl acetate and polyallylmelamine; crosslinked epoxide resins; polyacetals; polyalkylene oxides and polyphenylene oxides; polyamides, polyimides, polyamide/polyimide block copolymers, polysulfones and polyesters; and alkyd resins, for example glycerol/phthalic acid resins and mixtures thereof with melamine/formaldehyde resins, melamine/formaldehyde, urea/formaldehyde and phenol/formaldehyde resins and the like.

The compositions of matter and reaction products according to the invention, in particular the polymers, are especially used for producing electrically conductive coatings or patterns, in particular printed circuits. For this purpose, the metal ions in the compositions of matter or the at least partly complexed reaction products are reduced to zero-valent non-conductive metal nuclei (non-conductive visible image points) under the action of light in a manner which is known per se, or, in the case of compositions of matter or reaction products which contain no metal salts or metal ions, free radicals are obtained, on which electrically conductive metallic coatings or patterns can then be produced by electroless deposition of metals, such as copper and nickel and the like, in the customary manner. If desired, these metallic coatings or patterns can be thickened by electrolytic deposition of metals using conventional metal deposition baths. Any suitable light sources, for example xenon lamps, metal halide lamps and, in particular, high-pressure and medium-pressure mercury lamps, can be used for exposing the compositions of matter or reaction products according to the invention to light.

EXAMPLE 1

6 g (18.22 mmol) of ethyl 3-nitrothioxanthone-1-carboxylate, 8.12 g (91.1 mmol) of 2-nitropropane, 7.55 g (54.66 mmol) of potassium carbonate and 20 ml of N,N-dimethylformamide (DMF) are stirred at 50° C. for 2 hours. The mixture is concentrated in a rotary evaporator. The residue is brought to pH 6 with hydrochoric acid and extracted with methylene chloride. The organic extracts are washed with saturated NaCl solution, dried over sodium sulfate and evaporated. 5.95 g (88% of theory) of ethyl 3-(2-nitro-2-propyl)-thioxanthone-1-carboxylate are obtained by recrystallisation from toluene; melting point: 198°–201° C.

Analysis for $C_{19}H_{17}NO_5S$ (molecular weight 371.41): Calculated; C 61.45, H 4.62, N 3.77, O 21.54, S 8.63%. Found; C 61.52, H 4.54, N 4.02, O 24.73, S 8.62%.

3.0 g (8.07 mmol) of ethyl 3-(2-nitro-2-propyl)thioxanthone-1-carboxylate are hydrogenated with 1 g of Raney nickel in 90 ml of dioxane at 25° C. under 4 bar for 24 hours. The mixture is filtered and the mother liquor is concentrated. The residue is dissolved in 50 ml of tetrahydrofuran/toluene (1:1) and the solution is extracted with 2N HCl solution. The HCl extracts are separated off, brought to pH 7–8 with NaHCO₃ solution and extracted with tetrahydrofuran/toluene. The organic extracts are washed with saturated NaCl solution, dried over sodium sulfate and evaporated. Drying the residue under a high vacuum gives 2.3 g (83% of theory) of partly crystalline ethyl 3-(2-amino-2-propyl)-thioxanthone-1-carboxylate.

Analysis for $C_{19}H_{19}NO_3S$ (molecular weight 341.43): Calculated; C 66.84, H 5.61, N 4.10, O 14.06, S 9.39%. Found: C 67.53, H 6.32, N 3.87, O 13.87, S 8.52%.

3-(2-Nitro-2-propyl)-thioxanthone (melting point 131°–133° C., yield 40%) is obtained analogously from 3-nitrothioxanthone and is reacted as above to give 3-(2-amino-2-propyl)-thioxanthone, melting point: 265°–270°, yield: 51%.

Analysis for $C_{16}H_{15}NOS$ (molecular weight 269.36): Calculated; C 71.35, H 5.61, N 5.20, O 5.94, S 11.90%. Found; C 70.64, H 5.72, N 5.17, O 6.24, S 11.62%

3-(2-Nitro-2-propyl)-7-methyl-thioxanthone (melting point 170°–173° C., yield 64%) is obtained analogously from 3-nitro-7-methylthioxanthone, and is reacted as above to give 3-(2-amino-2-propyl)-7-methylthioxanthone (brownish oil), yield: 22%.

Analysis for $C_{17}H_{17}NOS$ (molecular weight 283.39): Calculated; C 72.05, H 5.34, N 4.94%. Found; C 72.41, H 5.50, N 4.82%.

EXAMPLE 2

2-bromomethyl-thioxanthone is prepared in accordance with the instructions of C. Valiliu et al., Rev. Chim. (Bukarest), 19, 561 (1968); melting point: 193°–196° C., analysis: Calculated; C 55.10; H 2.97, Br 26.18%, Found; C 54.12, H 3.06, Br 26.09%.

10 g (0.0328 mol) of 2-bromomethylthioxanthone and 2.13 g (0.0328 mol) of NaN₃ are dissolved in 50 ml of N,N-dimethylformamide and the solution is stirred at 50° C. for 12 hours. The course of the reaction is monitored by IR spectroscopy. The reaction has ended when no further increase in the band at 2,100 cm$^{-1}$ occurs. The mixture is allowed to cool, ice-water is added and the 2-azidomethyl-thioxanthone is separated off by filtration and washed several times with water. Yield: 6.80 g (77.5% of theory).

Melting point: 121°–123° C., analysis:

Calculated; C 69.89, H 4.60, N 5.18%. Found; C 68.91, H 4.40, N 5.35%.

5 g of 2-azidomethylthioxanthone are dissolved in 50 ml of N,N-dimethylformamide, and 0.5 g of Pd-on-charcoal is added, in an autoclave. Hydrogen is then passed in. The reaction is monitored by means of IR spectroscopy. It has ended when the band at 2,100 cm$^{-1}$ has disappeared. The reaction mixture is diluted with N,N-dimethylformamide, heated to 60° C. and filtered, the filtrate is cooled and water is added. The crystals which have precipitated are separated off by filtration and dried. 4.3 g (95.3% of theory) of 2-aminomethylthioxanthone are obtained. Melting point: 134°–136° C.

Analysis: calculated: C 69.69, H 5.81%. found; C 69.52, H 5.73%.

EXAMPLE 3

1.78 g of a polyethylene glycol diglycidyl ether with an epoxide equivalent of 2.64 mequivalent/g, 11.4 g of bisphenol A, 14.89 g of bisphenol A diglycidyl ether and 0.12 g of N,N-dimethylbenzylamine are added to 2 g (0.0166 mol) of 2-aminomethylthioxanthone in 50 ml of ethylene glycol monomethyl ether and the mixture is refluxed. After 5 hours, the mixture is allowed to cool to room temperature and the polymer is precipitated in water.

Yield: 25.4 g (93% of theory). [η]=0.14 dl/g (0.5% by weight in tetrahydrofuran at 25° C.). Glass transition point=56° C. Sulfur content: 1.65% (calculated: 1.7%).

EXAMPLE 4

5 g (0.0207 mol) of 2-aminomethylthioxanthone and 17.55 g of a polyadduct of bisphenol A and bisphenol A diglycidyl ether with glycidyl end groups and an epoxide equivalent of 842.2 are dissolved in 76 ml of ethylene glycol monoethyl ether and the solution is stirred under reflux for 6 hours. 16.8 g (74.5% of theory) of polymer are isolated by precipitation in water.

N contents: calculated: 1.29%, found: 1.26%.
Glass transition point=77.24° C.

EXAMPLE 5

3 g (0.00879 mmol) of ethyl 3-(2-amino-2-propyl)thioxanthone-1-carboxylate and 7.44 g of a polyadduct of bisphenol A and bisphenol A diglycidyl ether with glycidyl end groups and an epoxide equivalent of 842.2 are stirred in 50 ml of diethylene glycol dimethyl ether under nitrogen at 160° C. for 4 hours. The polymer is then isolated by precipitation in water. Yield: 9.38 g (89.8% of theory). Glass transition point=83.9° C.; average molecular weight=4,600 Daltons (determined by osmometry).

EXAMPLE 6

To test the photosensitivity, in each case 6 g of the polymers shown in the table which follows are dissolved in 20 ml of N,N-dimethylformamide, and 110 mg of copper-II acetate and 10 mg of $CuBr_2$ are added. This solution is applied onto a polyester foil with a doctor rod (wet film thickness 50 μm) and, after the film has been dried at 50° C. in a circulating air oven for 60 minutes, it is exposed to a 5 kW high-pressure mercury lamp through a mask (21-step sensitivity guide from Stouffer). The image visible after the exposure is thickened to a metallic, electrically conductive pattern at 49° C. in a copper bath composed of 12 g of $CuSO_4.5H_2O$/liter, 8 g of formaldehyde/liter, 15 g of NaOH/liter, 14 g of sodium potassium tartrate/liter, 20 g of ethylenediaminetetraacetic acid/liter and 1 g of octylphenol polyethylene glycol ether/liter (n~1, Triton×100 ® from Rohm and Haas). The results are shown in the following table.

TABLE

| Polymer according to Example No. | Exposure time/minute | Exposure temperature °C. | Last step defined |
|---|---|---|---|
| 3 | 3 | 90 | 5 |
| 4 | 3 | 80 | 6 |
| 5 | 3 | 90 | 4 |

What is claimed is:

1. A compound of the formula I

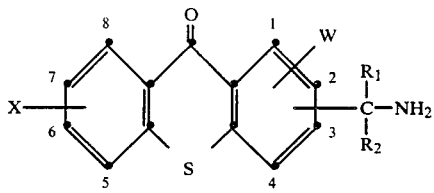

in which X is hydrogen, chlorine, bromine, $C_{1-4}$-alkyl or $C_{1-6}$-alkoxy, $R_1$ is hydrogen, $C_{1-6}$-alkyl, phenyl, —$COOCH_3$ or —$COOC_2H_5$ and $R_2$ is hydrogen, $C_{1-6}$-alkyl, —$COOCH_3$ or —$COOC_2H_5$, or $R_1$ and $R_2$ together are —$(CH_2)_e$—, where e=4 or 5, and W is hydrogen or —$COOC_{1-4}$-alkyl.

2. A compound of the formula I according to claim 1, in which X is hydrogen or chlorine or methyl bonded in the 7-position, the group —$C(R_1)(R_2)$—$NH_2$ is bonded in the 2-, 3- or 4-position, $R_1$ and $R_2$ independently of one another are hydrogen, methyl, ethyl, —$COOCH_3$ or —$COOC_2H_5$ and W is hydrogen, —$COOCH_3$ or —$COOC_2H_5$.

3. A compound of the formula I according to claim 1, in which X is hydrogen or methyl bonded in the 7-position, the group —$C(R_1)(R_2)$—$NH_2$ is bonded in the 2- or 3-position, $R_1$ and $R_2$ are each hydrogen or methyl and W is hydrogen, —$COOCH_3$ or —$COOC_2H_5$.

4. 2-Aminomethylthioxanthone, 3-(2-amino-2-propyl)-thioxanthone, 3-(2-amino-2-propyl)-7-methyl-thioxanthone and ethyl 3-(2-amino-2-propyl)-thioxanthone-1-carboxylate according to claim 1.

5. Photosensitive compositions of matter which are capable of undergoing condensation or addition reactions, containing (1) a thioxanthone of the formula I

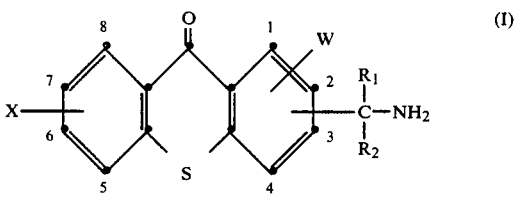

in which X is hydrogen, chlorine, bromine, $C_{1-4}$-alkyl or $C_{1-6}$-alkoxy, $R_1$ is hydrogen, $C_{1-6}$-alkyl, phenyl, —$COOCH_3$ or —$COOC_2H_5$ and $R_2$ is hydrogen, $C_{1-6}$-alkyl, —$COOCH_3$ or —$COOC_2H_5$, or $R_1$ and $R_2$ together are —$(CH_2)_e$—, where e=4 or 5, and W is hydrogen or —$COOC_{1-4}$alkyl, (2) one or more compounds selected from di- to polyglycidyl ethers of phenol novolaks and cresol novolaks and compounds of the formulae XI to XIII

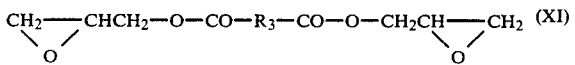

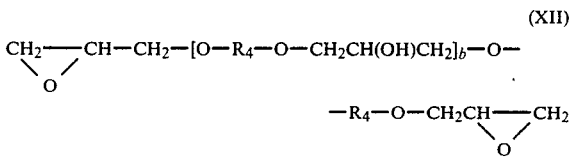

and

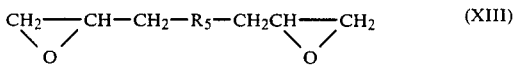

and, in the further presence or absence of, compounds of the formulae XIV, XV and/or XVI

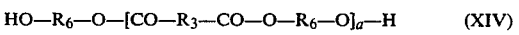

and/or

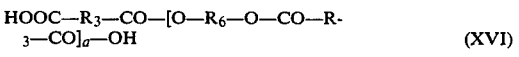

the proportion of compounds of the formulae XIV, XV and/or XVI being at most 80 mole %, based on all the reactants mentioned under (2)

(3) in the presence or absence of a crosslinking agent and (4) in the presence or absence of a salt of a metal of group Ib or VIII of the Periodic Table, in which a is a number form 1 to 100, b is a number from 0 to 150, $R_3$ is a direct bond, —$C_mH_{2m}O$, where m=2-12, or cyclohexylene, cyclohexenylene, phenylene or endomethylenecyclohexenylene, each of which is unsubstituted or substituted by a methyl group, R$_4$ is —C$_m$H$_{2m}$—, where m=2-12, phenylene,

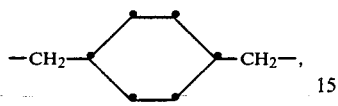

or a group of the formula

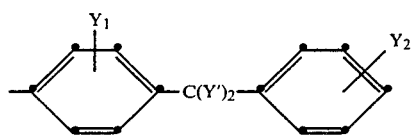

or —(Y$_3$O)$_o$—Y$_3$— Y' is hydrogen or methyl, Y$_1$ and Y$_2$ independently of one another are hydrogen, chlorine or bromine, Y$_3$ is —(CH$_2$)$_2$—, —CH$_2$CH(CH$_3$)— or —(CH$_2$)$_4$—, o is a number from 1 to 50, R$_5$ is

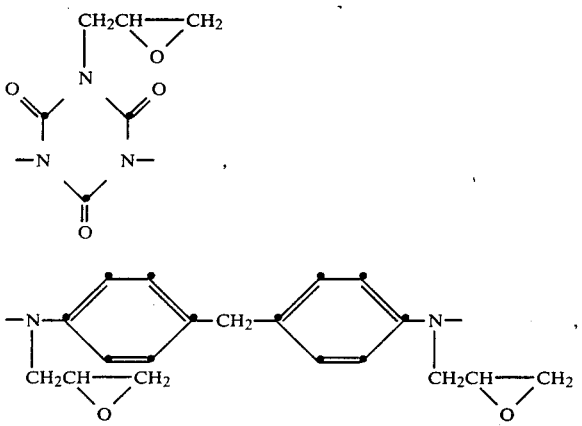

or the radical of ethylene-urea, 1,3-propylene-urea, 5,5-dimethylhydantoin, 2-hydroxyethyl-5,5-dimethylhydantoin or 2-hydroxypropyl-5,5-dimethylhydantoin and R$_6$ is —C$_m$H$_{2m}$—, where m=2-12, —(CH$_2$CH$_2$O)$_r$—CH$_2$CH$_2$, where r=1-40, —CH(CH$_3$)CH$_2$OCH$_2$CH(CH$_3$)—, —CH$_2$—C(CH$_3$)$_2$—OCO—C(CH$_3$)$_2$CH$_2$—, cyclohexylene,

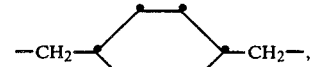

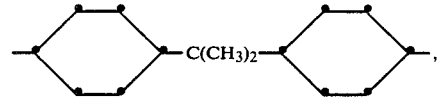

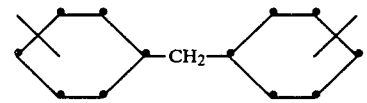

naphthylene or biphenylene, or phenylene which is unsubstituted or substituted by a methyl, methoxy or nitro group.

6. A composition of matter according to claim 5, in which X is hydrogen or chlorine or methyl bonded in the 7-position, the group —C(R$_1$)(R$_2$)—NH$_2$ is bonded in the 2-, 3- or 4-position, R$_1$ and R$_2$ independently of one another are hydrogen, methyl, ethyl, —COOCH$_3$ or —COOC$_2$H$_5$ and W is hydrogen, —COOCH$_3$ or —COOC$_2$H$_5$.

7. A composition of matter according to claim 5, containing a thioxanthone of the formula I in which X is hydrogen or methyl bonded in the 7-position, the group —C(R$_1$)(R$_2$)—NH$_2$ is bonded in the 2- or 3-position, R$_1$ and R$_2$ are each hydrogen or methyl and W is hydrogen, —COOCH$_3$ or —COOC$_2$H$_5$, one or more compounds selected from di- and/or tri-glycidyl ethers of phenol novolaks or cresol novolaks, triglycidylisocyanurate, diglycidylhexahydrophthalate, N,N'-diglycidyl-5,5-dimethylhydantoin, N-glycidyl-N'-2-hydroxyethylglycidyl-5,5-dimethylhydantoin and/or N-glycidyl-N'-2-hydroxy-propylglycidyl-5,5-dimethylhydantoin and compounds of the formulae (A), (B) and (C)

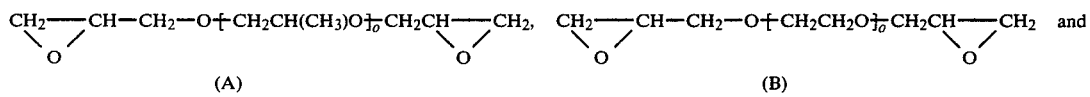

(A) (B)

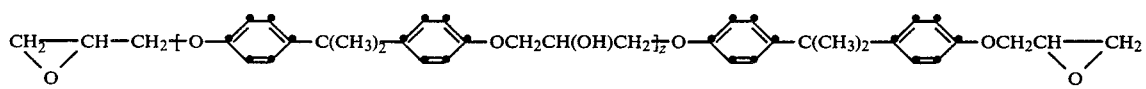

(C)

and in which o equals 2-40, and z equals 0.1-13.

8. A composition of matter according to claim 5, containing, as the compound of the formula 1, 2-aminomethylthioxanthone, 3-(2-amino-2-propyl)-thioxanthone, 3-(2-amino-2-propyl)-7-methylthioxanthone or ethyl 3-(2-amino-2-propyl)thioxanthone-1-carboxylate, a compound of the formula (A) or (B)

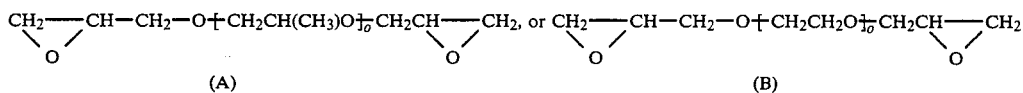

(A)    (B)

mixed with a compound of the formula C)

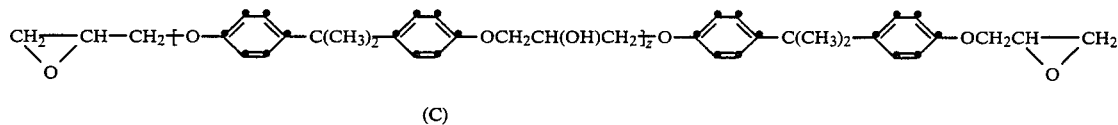

(C)

and in which o is 2–20 and z is 2–11.

9. A composition of matter according to claim 5, containing, as the compound of the formula I, 2-aminomethylthioxanthone, 3-(2-amino-2-propyl)-thioxanthone, 3-(2-amino-2-propyl)-7-methylthioxanthone or ethyl 3-(2-amino-2-propyl)thioxanthone-1-carboxylate, N,N'-diglycidyl-5,5-dimethylhydantoin, N-glycidyl-N'-2-hydroxyethyl-glycidyl-5,5-dimethyldantoin and/or N-glycidyl-N'-2-hydroxypropylglycidyl-5,5-dimethylhydantoin, mixed with a compound of the formula (C)

and in which o is 2–20 and z is 2–11.

10. A composition of matter according to claim 5, which contains an iron, cobalt, nickel or copper salt.

11. A composition of matter according to claim 5, which contains copper-II acetate or a mixture of copper-II acetate and copper-II bromide.

12. A composition of matter according to claim 5, which contains hexahydrophthalic anhydride or bisphenol A as the crosslinking agent.

13. A composition of matter according to claim 7, in which o equals 2–40 and z equals 2–11.

* * * * *

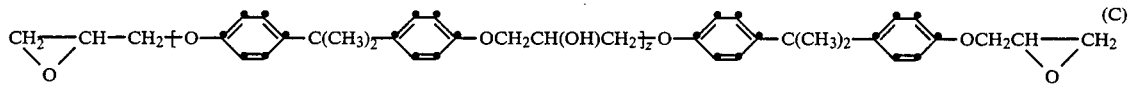

(C)